(12) United States Patent
Fuerst et al.

(10) Patent No.: US 11,090,122 B2
(45) Date of Patent: Aug. 17, 2021

(54) SYSTEMS AND METHODS FOR MAGNETIC SENSING AND DOCKING WITH A TROCAR

(71) Applicant: Verb Surgical Inc., Mountain View, CA (US)

(72) Inventors: Bernhard A. Fuerst, Sunnyvale, CA (US); Dennis Moses, Hollywood, FL (US); Miguel Piedrahita, Palo Alto, CA (US); Michael Wong, Sunnyvale, CA (US); Pablo Garcia Kilroy, Menlo Park, CA (US); Jose Luis Cordoba, Malaga (ES)

(73) Assignee: VERB SURGICAL INC., Santa Clara, CA (US)

( * ) Notice: Subject to any disclaimer, the term of this patent is extended or adjusted under 35 U.S.C. 154(b) by 251 days.

(21) Appl. No.: 16/285,001

(22) Filed: Feb. 25, 2019

(65) Prior Publication Data
US 2020/0268453 A1 Aug. 27, 2020

(51) Int. Cl.
*A61B 34/20* (2016.01)
*B25J 13/08* (2006.01)
(Continued)

(52) U.S. Cl.
CPC .......... *A61B 34/20* (2016.02); *A61B 17/3423* (2013.01); *A61B 34/35* (2016.02); *B25J 13/088* (2013.01); *B25J 15/0019* (2013.01); *A61B 2017/00477* (2013.01); *A61B 2034/2051* (2016.02); *A61B 2562/0223* (2013.01); *B25J 9/1689* (2013.01)

(58) Field of Classification Search
CPC ......... A61B 34/20; A61B 34/35; A61B 34/37; A61B 34/30; A61B 17/3423; A61B 2034/2051; A61B 2034/2053; A61B 2034/301–305; A61B 2034/2046; A61B 2017/00477; A61B 2562/0223; B25J 13/088; B25J 15/0019; B25J 9/1689
See application file for complete search history.

(56) References Cited

U.S. PATENT DOCUMENTS

| | | | |
|---|---|---|---|
| 2009/0043246 A1* | 2/2009 | Dominguez | H01F 7/0252 604/21 |
| 2013/0298715 A1 | 11/2013 | Valdastri et al. | |

(Continued)

OTHER PUBLICATIONS

International Search Report and Written Opinion for Application No. PCT/US2019/021465, dated Oct. 29, 2019.
(Continued)

*Primary Examiner* — Erich G Herbermann
(74) *Attorney, Agent, or Firm* — Womble Bond Dickinson (US) LLP

(57) ABSTRACT

A surgical robotic system has a tool drive coupled to a distal end of a robotic arm that has a plurality of actuators. The tool drive has a docking interface to receive a trocar. One or more sensors in the docking interface sense a magnetic field generated by the trocar. One or more processors are configured to determine a position and orientation of the trocar based on the sensed magnetic field, and then drive the actuators to orient the docking interface to the determined orientation of the trocar, or otherwise guide the robotic arm toward the determined position of the trocar. Other aspects are also described and claimed.

20 Claims, 13 Drawing Sheets

(51) Int. Cl.
    *B25J 15/00*     (2006.01)
    *A61B 34/35*     (2016.01)
    *A61B 17/34*     (2006.01)
    *B25J 9/16*     (2006.01)
    *A61B 17/00*     (2006.01)

(56) References Cited

U.S. PATENT DOCUMENTS

| | | |
|---|---|---|
| 2014/0275955 A1 | 9/2014 | Crawford et al. |
| 2018/0283842 A1 | 10/2018 | Rueb et al. |
| 2018/0289431 A1 | 10/2018 | Draper et al. |
| 2019/0053824 A1 | 2/2019 | Scheib |
| 2019/0183585 A1* | 6/2019 | Rafii-Tari ............... A61B 34/30 |
| 2019/0321115 A1 | 10/2019 | Anderson et al. |

OTHER PUBLICATIONS

An Improved 6-D Pose Detection Method Based on Opposing-Magnet Pair System and Constraint Multiple Magnets Tracking Algorithm; IEEE Sensors Journal, vol. 17, No. 20, Oct. 15, 2017, by Shuang Song, Xiaoxiao Qiu, Wei Liu, and Max Q-H. Meng; 2017: 8 pages.

Tracking Position and Orientation of Magnetic Objects Using Manetometer, by Niklas Whalstrom and Fredrik Gustafsson; Linköping University Post Print <http://urn.kb.se/resolve?urn=urn:nbn:se:liu:diva-122395> 14 pages; 2015.

* cited by examiner

SYSTEMS AND METHODS FOR MAGNETIC SENSING AND DOCKING WITH A TROCAR

TECHNICAL FIELD

This disclosure relates generally to the field of robotic surgery and, more particularly, to docking systems for surgical robotics or for use in robotic-assisted surgical systems.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one endoscopic camera through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery. In some embodiments, MIS may be performed with robotic systems that include one or more robotic arms for manipulating surgical instruments based on commands from an operator.

In MIS procedures, access is provided to the body cavity of a patient through a trocar. Once a distal end of a cannula of the trocar is properly positioned and inserted through tissue and into an interior region of the patient, for example, through the abdominal wall of the patient, a surgical robotic arm having a trocar docking interface at its distal end, or a tool drive attached thereto, is manually maneuvered by a user until the docking interface is aligned with an attachment portion (e.g., a mating interface) on the proximal end of the trocar (outside the patient.) The user then latches the trocar mating and the docking interface to each other, either manually or as an automated step, thereby rigidly attaching the arm to the trocar. A surgical tool having an end effector at its distal end (e.g., scissors, grasping jaws, or camera) is then inserted into a top opening of the cannula and the tool is then attached to the arm such that further surgical operations can be performed with the tool.

SUMMARY

In MIS procedures, once a cannula of a trocar is properly positioned and inserted through tissue and into an interior region of a patient, it is desirable to dock a robotic arm, or a tool drive attached thereto, to the trocar to provide a rigid mechanical attachment of the robotic arm and the trocar. Such attachment of the robotic arm and the trocar can, for example, provide stabilization of the trocar such that one or more surgical tools can be inserted through a lumen of the cannula and into the interior region of the patient. In this regard, a docking interface located on a distal block of the robotic arm/tool drive is maneuvered until the docking interface is aligned with an attachment portion (e.g., a mating interface) on a portion of the trocar exposed outside the patient. The docking interface of the robotic arm/tool drive is then latched to the attachment portion of the trocar to provide the rigid mechanical attachment of the robotic arm/tool drive and the trocar.

Systems and methods of docking of robotic arms to trocars are needed that obviate the challenges presented by some modalities of trocar docking. For example, manually docking a robotic arm/tool drive with a trocar can be difficult due to the precise alignment required between the trocar and the robotic arm or the attached tool drive. As another example, some trocar docking procedures employ optical tracking through the use of visual sensors that guide the robotic arm to the trocar. However, visual sensors can be blocked by sterile barriers or drapes that are sometimes used with robotic arms and in a surrounding environment. Additional examples of trocar docking procedures, for example, ultrasonic triangulation, inertial sensing, and the detection of generated electromagnetic fields, involve the use of electrically-powered components on the trocar that generate signals that can be used to guide the robotic arm. However, such electrically-powered equipment can reduce the lifespan of a trocar, as these components can degrade, for example, due to repeated use or through sterilization procedures.

The use of magnets, for example, non-electrically powered magnets such as permanent magnets, in the trocar can provide magnetic fields for sensing by a sensor system such that the robotic arm can be controlled to automatically align with a pose, e.g., a spatial position and orientation, of the trocar and can be guided or driven into mechanical coupling with the trocar with accuracy and precision. The use of such magnetic sensing does not require a line-of-sight between the robotic arm and the trocar so that, for example, sterile barriers can be used to cover portions of the robotic arm without interfering with trocar docking procedures. In addition, the use of magnets in the trocar to generate the magnetic field for docking the robotic arm does not require electrically-powered components such that the trocar is provided with a robust configuration that increases the lifespan and versatility of the trocar.

Generally, in one aspect, a surgical robotic system can include a robotic arm with a plurality of actuators, and a tool drive coupled to a distal end of the robotic arm. The tool drive can comprise a docking interface to receive a mating interface or attachment portion of a trocar. The system also comprises one or more sensors that are operable to sense a magnetic field generated by the trocar. One or more processors are configured to determine a position and an orientation of the trocar based on the sensed magnetic field. The processors are also configured to drive the robotic arm actuators to orient the docking interface to the determined orientation of the attachment portion of the trocar and to guide the robotic arm toward the determined position of the attachment portion of the trocar.

In one variation, the robotic arm is automatically driven toward the determined position of the trocar by one or more actuators controlled by the one or more processors. In another variation, the robotic arm is manually guided (e.g., forced by a hand of the user) toward the determined position of the trocar while being assisted by the actuators that are controlled by the one or more processors. In still another variation, the robotic arm is manually guided by a user toward the determined position of the trocar, and one or more actuators being controlled by the one or more processors resists the user's manual force on the robotic arm when the user's manual force is directing the robotic arm away from the determined position of the trocar.

The docking interface can define a chamber and a receiving space positioned between one or more clamp components in the chamber. In one variation, the one or more clamp components is movably coupled to the docking interface and configured to move to secure the attachment portion of the trocar, such as an upper protrusion, in the docking interface. In another variation, a lever is supported on the docking interface, and movement of the lever causes movement of the one or more clamp components toward a locked or unlocked position. In still another variation, a switch is provided that, when actuated, signals the processors to activate the one or more sensors and/or to determine the position and orientation of the trocar based on the sensed magnetic field (and to then drive the actuators to guide the docking interface toward the determined position of the trocar and to orient the docking interface to the determined orientation of the trocar.) The switch can be positioned such that movement of the lever actuates the switch.

According to one variation, the one or more sensors is a plurality of sensors in the chamber of the docking interface that can include at least three sensors disposed at respective different depths measured from a frontal opening of the docking interface.

In another variation of the disclosure, the one or more sensors comprises a first plurality of sensors coupled to a first sensor board and a second plurality of sensors coupled to a second sensor board, with the first sensor board and the second sensor board on opposite sides of a chamber of the docking interface.

According to the present disclosure, a method for docking a robotic arm of a surgical robotic system to a trocar is provided. The method can include measuring a magnetic field generated by a pair of magnets embedded in the trocar to produce a measured sensor reading. The measurement can be performed by a plurality of sensors that are coupled to a docking interface of a tool drive coupled to the robotic arm.

One or more processors can determine (e.g., select as an initial guess) an estimated pose of the trocar that includes a position and orientation of the trocar, e.g., 6 degrees of freedom (DOF) including 3 DOF with regard to position and 3 DOF with regard to orientation. This estimated trocar pose may be in relation to a known pose of the docking interface (also referred to here as a "transform"). In addition, the one or more processors calculate an estimated sensor reading based on the estimated pose of the trocar, a known placement of the pair of magnets that includes a known position of the magnets relative to each other and a known offset between respective axes of polarity of the magnets, and a physical or deterministic model of the sensors in the docking interface.

A similarity measure or difference is then computed by the one or more processors, which in effect compares the estimated sensor reading to a measured (or real) sensor reading taken from the sensors. This similarity measure is then used by the processor to produce an updated transform (an update to the estimated trocar pose, in relation to the docking interface pose.)

The one or more processors then repeat the operation above of calculating an estimated sensor reading, this time using the updated (estimated) trocar pose, which results in an updated (estimated) sensor reading. A new similarity measure is then computed based on the updated sensor reading and the measured (real) sensor reading. This loop is repeated, which should lead to progressively greater measures of similarity, thereby "optimizing" or adapting the estimated trocar pose until the difference between the updated sensor reading and the measured sensor reading is lower than a threshold error, resulting in an updated sensor reading corresponding to a "final" or determined trocar pose. Upon completion of this optimization algorithm, such that the threshold error is no longer being exceeded, the measured sensor reading or the optimized estimated sensor reading can be used, for example, in guiding the robotic arm to move the docking interface closer to the trocar, as representing the final or determined pose of the trocar.

The method can also include guiding the robotic arm such that the docking interface reaches a ready to dock or docked state or pose (position and orientation), based on the updated estimated sensor reading of the pose of the trocar. The ready to dock or docked state may be a pose of the docking interface that is sufficiently close to a pose of the trocar, for example so that a mechanical latch or clamp in the docking interface can engage with an attachment portion of the trocar. The ready to dock state can be identified by the one or more processors when the signals associated with the pose of the docking interface match the optimized or updated estimated sensor readings, i.e., are within an acceptable range of tolerance thereof. In one variation, the ready to dock or docked state of the docking interface relative to the trocar can be visually determined by an operator.

In one variation, the robotic arm is automatically driven toward the trocar by one or more actuators controlled by the one or more processors. In another variation, the robotic arm is manually guided (e.g., forced by a hand of the user) toward the trocar while being assisted by the actuators that are controlled by the one or more processors. In still another variation, the robotic arm is manually guided toward the trocar and the actuators being controlled by the one or more processors resists the user's manual force on the robotic arm while the user's manual force is directing the robotic arm away from the trocar.

In one aspect, docking of the docking interface with the trocar comprises guiding the docking interface toward the trocar until ready to dock or docked state is reached, which may be when an attachment portion of the trocar is just outside of or at least partially disposed in a chamber of the docking interface.

In another variation, the docking interface comprises a lever operable manually by a user to lock or latch the trocar to the docking interface (in the ready to dock or docked state). A switch can be provided that is in electronic communication with the one or more processors. Moving the lever rearwardly, toward an unlocked position, can cause contact with the switch to signal the one or more processors to activate and obtain readings from the plurality of sensors and to effect guidance of the robotic arm toward the trocar. The lever can also be moved forwardly to move one or more clamp components in the docking interface to lock or latch the docking interface to the trocar.

DETAILED DESCRIPTION

Non-limiting examples of various aspects and variations of the invention are described herein and illustrated in the accompanying drawings.

Figure 1:
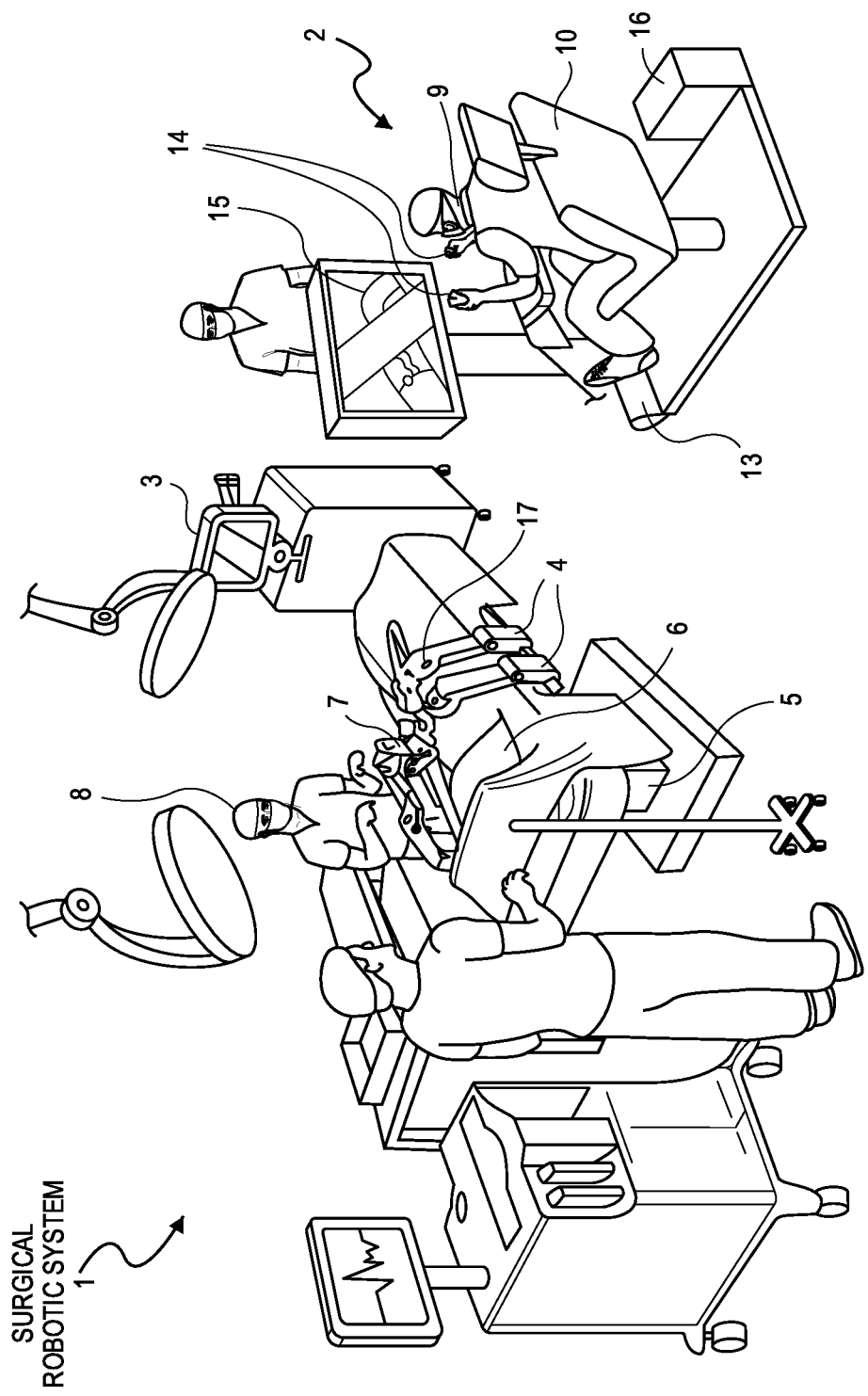
FIG. 1 is an overview schematic of an operating room arrangement with a surgical robotic system.

Referring to FIG. 1, this is a pictorial view of an example surgical robotic system 1 in an operating arena. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted on a cart, ceiling or sidewall, or in another suitable structural support.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), prior to initiating surgery with the surgical robotic system 1, the surgical team can perform the preoperative setup. During the preoperative setup, the main components of the surgical robotic system (table 5 and robotic arms 4, control tower 3, and user console 2) are positioned in the operating room, connected, and powered on. The table 5 and robotic arms 4 may be in a fully-stowed configuration with the arms 4 under the table 5 for storage and/or transportation purposes. The surgical team can extend the arms 4 from their stowed position for sterile draping, e.g., covering one or more portions of the system 1, such as portions of the arms 4, with a sterile barrier to minimize, inhibit, or prevent the transmission of pathogens. After draping, the arms 4 can be partially retracted until needed for use. A number of conventional laparoscopic steps may need to be performed including trocar placement and insufflation. For example, each trocar can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars or other tools or equipment.

In one embodiment, the remote operator 9 holds and moves the UID 14 to provide an input command to drive one or more robotic arm actuators 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control motions of the robotic arm actuators 17. The robotic system 1 may use control signals derived from the spatial state signals, to control proportional motion of the actuators 17. In one embodiment, a console processor of the console computer system 16 receives the spatial state signals and generates the corresponding control signals. Based on these control signals, which control how the actuators 17 are energized to drive a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn drives other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that are transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 6:
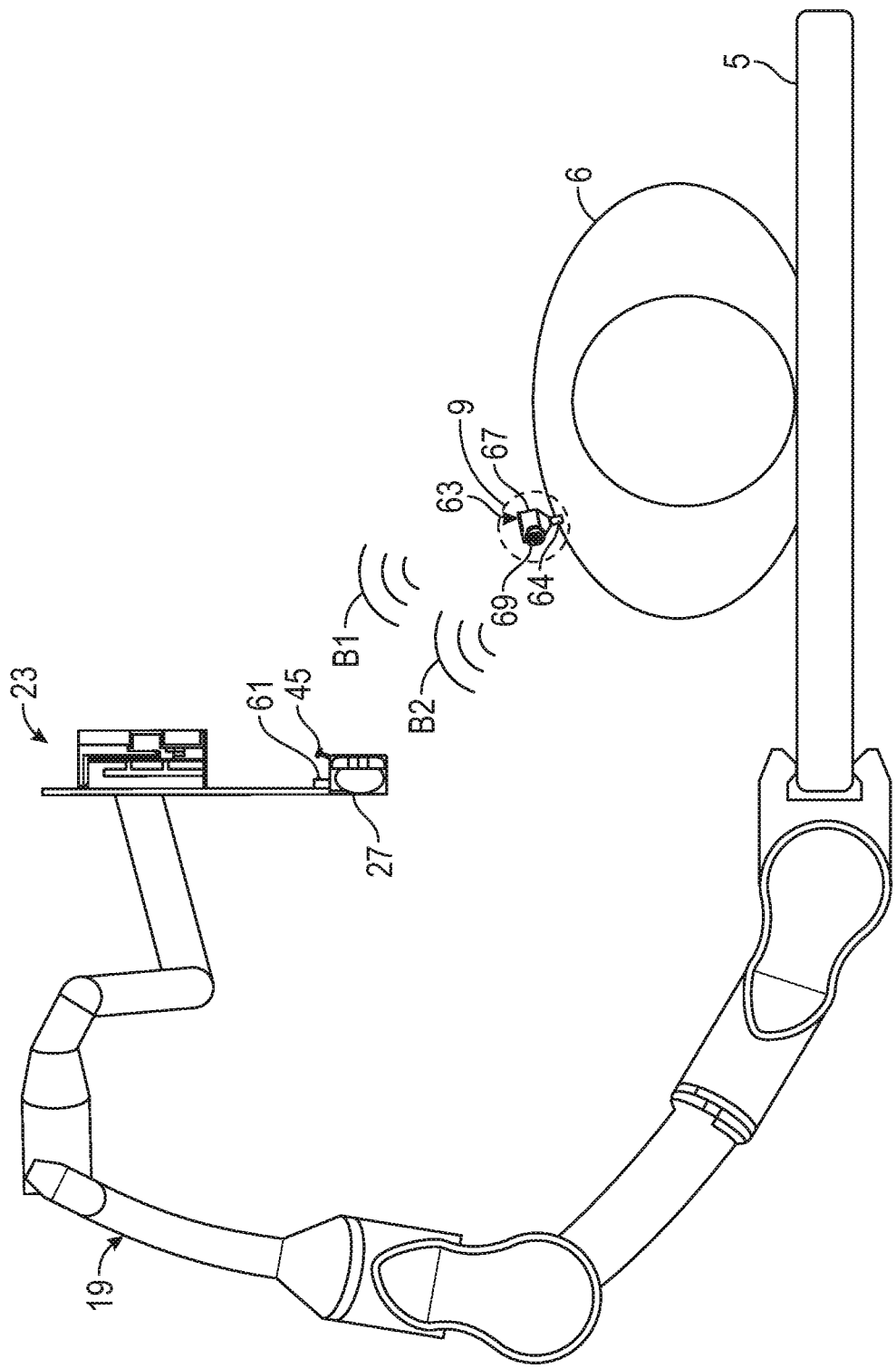
FIGS. 6-8 are pictorial views of operations of a method of docking a tool drive attached to a robotic arm of a surgical robotic system to a trocar according to one aspect of the disclosure.

As described above, to create a port for enabling introduction of a surgical instrument into the patient 6, a trocar assembly may be at least partially inserted into the patient through an incision or entry point in the patient (e.g., in the abdominal wall). The trocar assembly may include a cannula or trocar 63 (FIG. 6), an obturator, and/or a seal. In some variations, the trocar assembly can include an obturator such as a needle with a sharpened tip for penetrating through a patient's skin. The obturator may be disposed within the lumen of the trocar 63 when being inserted into the patient 6, and then removed from the trocar 63 such that a surgical instrument may be inserted through the lumen of the trocar 63. Once positioned within the body of the patient 6, the trocar 63 may provide a channel for accessing a body cavity or other site within the patient 6, for example, such that one or more surgical instruments or tools can be inserted into a body cavity of the patient 6, as described further herein. It will be understood that the trocar 63 as described herein includes at least a cannula, and can optionally include an obturator or other components.

Figure 2:
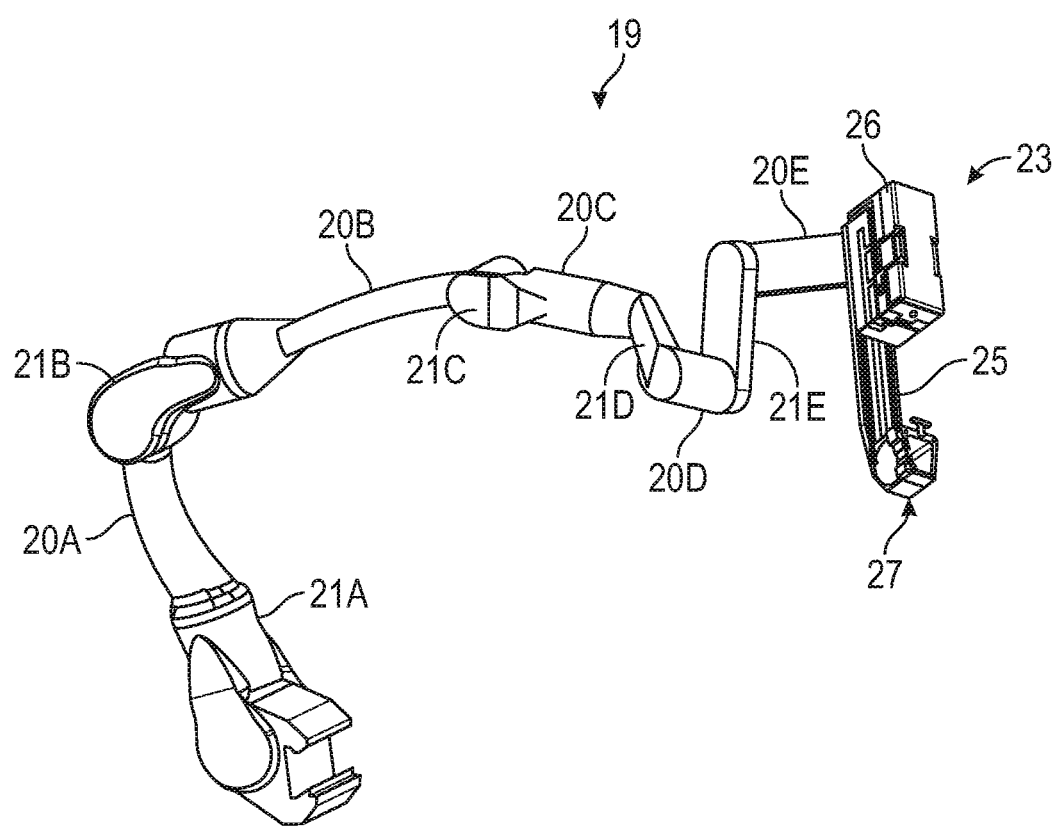
FIG. 2 is a perspective view of a portion of a robotic arm according to one aspect of the disclosure.

Turning to FIG. 2, a portion of a robotic arm 19 is illustrated according to one aspect of the disclosure. The robotic arm 19 and associated components described herein can form a surgical robotic system according to an embodiment of the disclosure. The robotic arm 19 can be incorporated into the surgical robotic system 1 described above, or can form a portion of a different system. While a single robotic arm 19 has been illustrated, it will be understood that the robotic arm 19 can include additional arm portions or can be a component of a multi-arm apparatus without departing from the disclosure.

The robotic arm 19 can include a plurality of links (e.g., links 20A-20E) and a plurality of joint modules (e.g., joints 21A-21E) for actuating the plurality of links relative to one another. The joint modules can include various joint types, such as a pitch joint or a roll joint, any of which can be actuated manually or by the robotic arm actuators 17, and any of which may substantially constrain the movement of the adjacent links around certain axes relative to others. As also shown, a tool drive 23 is attached to the distal end of the robotic arm 19. As described herein, the tool drive 23 can be configured with a docking interface 27 to receive an attachment portion (e.g., a mating interface) of a trocar 63 such that one or more surgical instruments (e.g., endoscopes, staplers, etc.) can be guided through a lumen of the cannula of the trocar 63. The plurality of the joint modules 21A-21E of the robotic arm 19 can be actuated to position and orient the tool drive 23 for robotic surgeries.

Figure 3:
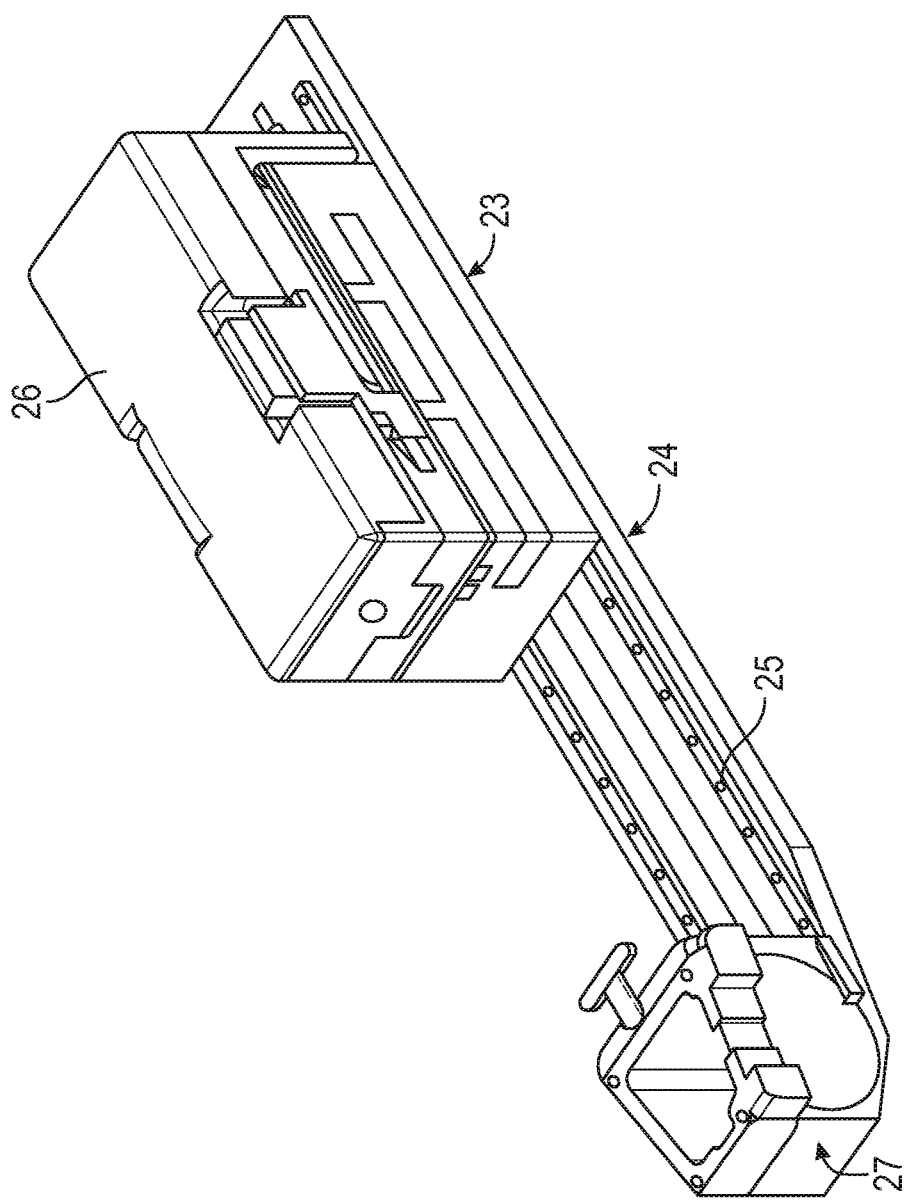
FIG. 3 is a schematic perspective view of a tool drive of the robotic arm of FIG. 2.

FIG. 3 is a schematic diagram illustrating an exemplary tool drive 23 without a loaded tool in accordance with aspects of the subject technology. In one variation, the tool drive 23 may include an elongated base (or "stage") 24 having longitudinal tracks 25 and a tool carriage 26, which is slidingly engaged with the longitudinal tracks 25. The stage 24 may be configured to couple to the distal end of a robotic arm 19 such that articulation of the robotic arm 19 positions and/or orients the tool drive 23 in space. The tool carriage 26 may be configured to receive a tool for extending through the trocar 63.

Additionally, the tool carriage 26 may actuate a set of articulated movements through a cable system or wires manipulated and controlled by actuated drives (the terms "cable" and "wire" are used interchangeably throughout this application). The tool carriage 26 may include different configurations of actuated drives, such as a mechanical transmission.

Figure 4:
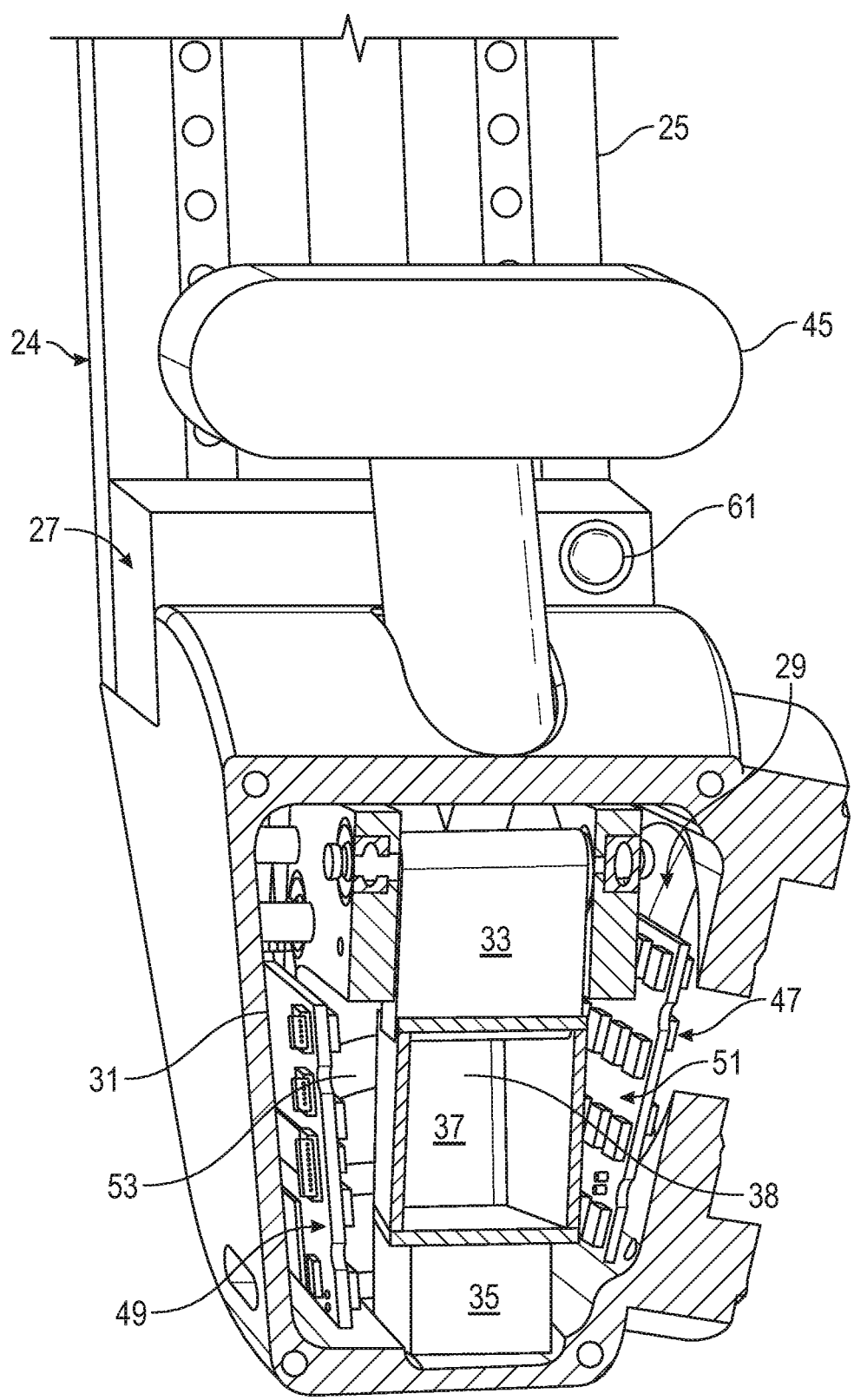
FIG. 4 is a perspective view of a docking interface of the tool drive of FIG. 3.

Referring additionally to FIG. 4, the trocar 63 can be coupled to the tool drive 23 or another component of the surgical robotic system 1 at a docking station or docking interface 27 located at a distal block of the elongated base 24. The docking interface 27 is configured to receive a portion of the trocar 63 such that the docking interface 27 is configured as a trocar docking interface, a trocar attachment device, or a trocar mounting device. The docking interface 27 can provide a reliable and quick way to attach the trocar 63 to the surgical robotic system 1.

The docking interface 27 can define a chamber 29 that is accessible through a mouth or frontal opening 31 of the docking interface 27 and which can include first and second clamp components 33, 35 (e.g., arms, plates, levers, members) arranged about a receiver 37 that defines a receiving space 38 for receiving a portion of the trocar 63 (e.g., a mating interface formed in an attachment portion of a cannula located in a proximal portion of the cannula). At least one of the clamp components 33, 35 may be pivotable between an open position and a closed position such that an attachment portion 69 of the trocar 63 can be inserted into the receiving space 38 between the clamp components 33, 35 so that a portion of the trocar 63 is held in place at least partially by the first and second clamp components 33, 35.

In one variation, the docking interface 27 may include an over-center mechanism such as a lever 45 or other suitable locking component that mechanically cooperates with the clamp component 33, for example, through a pin and slot arrangement or through another pivotable or movable connection, between the open and closed positions. The lever 45 can be movable, e.g., along a track or slot defined in a body or housing of the docking interface 27, between a forward, locked position (e.g., a locked over-center position) and a rearward, unlocked position. When the lever 43 is moved toward the locked position, the lever 45 may urge the clamp component 33 downwardly toward the receiving space 38 and lock the clamp component 33 in the closed position such that a portion of the trocar 63 is securely held between the first and second clamp components 33, 35. In some variations, second clamp component 35 can be stationary or can be fixed. In one variation, the lever 45 can be controlled and/or driven with an electric motor or actuator under manual or processor control.

In some variations, the docking interface 27 may also provide a sterile barrier between sterile components such as the trocar 63 and non-sterile components such as the first and second clamp components 33, 35 (or other non-sterile components of the surgical system). The sterile barrier may be provided, for example, by a sterile adapter formed of a surgical-grade polymer or other surgical-grade material that is interposed between the trocar 63 and the first and second clamp components 33, 35 (not shown for clarity of illustration).

Figure 5:
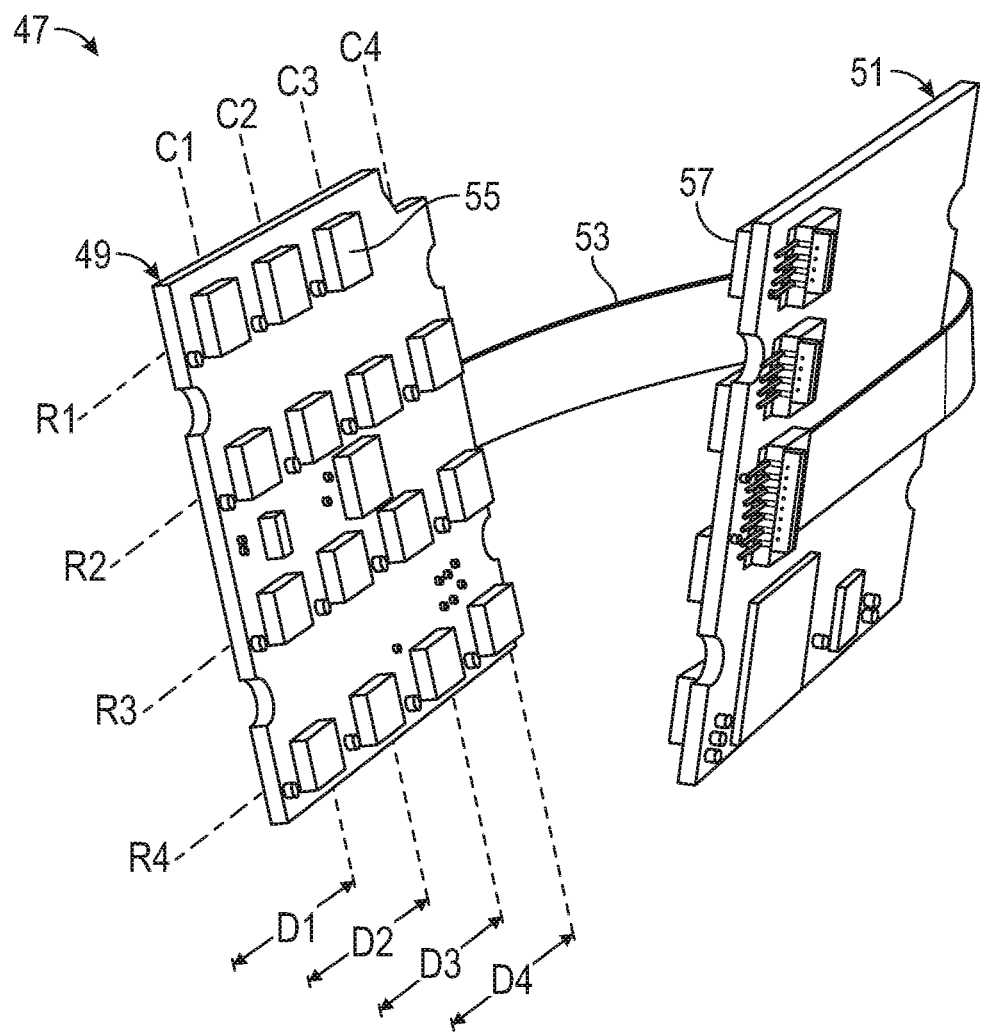
FIG. 5 is a perspective view of a sensor system of the docking interface of FIG. 4.

Referring additionally to FIG. 5, the docking interface 27 also includes a sensor system 47 that includes at least a motherboard or first sensor board 49 at a first location of the docking interface 27 and a daughterboard or second sensor board 51 at second location of the docking interface 27 and in electrical communication with the first sensor board 49 via a cable 53 or other electrically conductive connection. In one variation, communication between the sensor boards 49, 51 can employ a multi-slave and multi-master inter-integrated communication computer bus. One or both of the sensor boards 49, 51 can include a microprocessor or other associated processor, for example, to control and/or read the sensors of the sensor boards 49, 51 and to facilitate communication between the sensor boards 49, 51, e.g., to enable temporal synchronization between the sensor boards 49, 51. As shown, the first sensor board 49 and the second sensor board 51 are positioned spaced apart from but parallel to each other, e.g., facing each other, on opposite lateral sides of the chamber 29 of the docking interface 27. The first sensor board 49 includes a first plurality of sensors 55 and the second sensor board 51 includes a second plurality of sensors 57. In this regard, the sensors 55, 57 are embedded in or otherwise coupled to the robotic arm 19 or the tool drive 23. Each of the plurality of sensors 55, 57 are arranged such that at least one sensor 55, 57 is disposed rearward, e.g., at a depth measured from the frontal opening 31 of the docking interface 27, with respect to another respective sensor 55, 57. As shown, sensors 55, 57 are disposed at least at a first depth D1, a second depth D2, a third depth D3, and a fourth depth D4, with D4>D3>D2>D1. The depths D1, D2, D3, D4 can be spaced at uniform or non-uniform increments without departing from the disclosure. While the sensors 55, 57 have been described in a grid-like configuration of rows R1-R4 and columns C1-C4, it will be understood that one or both of the pluralities of sensors 55, 57 can have a different arrangement without departing from the disclosure.

As described further herein, the sensors 55, 57 are operable to sense or measure a magnetic field associated with the trocar 63, and produce respective corresponding electrical signals. In this regard, the sensors 55, 57 can be configured as magnetometers, e.g., sensors that receive at least a portion of a magnetic field as an input and produce an output electrical signal corresponding to a strength or other characteristic of the magnetic field, and such that the sensors 55, 57 can be transducers. Any of the sensors 55, 57 can be configured to receive a different physical input and produce a corresponding electrical signal, for example, inertial measurement units, accelerometers, etc. In this regard, the sensors 55, 57 produce an output electrical signal that can be electrically communicated to, for example, a processor or controller that is incorporated into the control tower 3 to provide force or velocity commands to direct a movement of the robotic arm 19 via the robotic arm actuators 17, as described further herein. It will be understood that a processor can be incorporated into additional or alternative portions of the surgical robotic system 1, and that the sensor system 47 can be in electrical communication with one or more different processors. A switch 61 or other control is mounted on or near the docking interface 27, for example, behind the lever 45 at a position such that the lever 45 can be urged into contact with the switch 61, as described further herein. The switch 61 can be in electrical communication with the processor in the control tower 3 to signal the processor to energize or activate one or both of the sensor boards 49, 51 to activate the sensor system 47 to sense or measure magnetic fields, and to effect guidance of the robotic arm 19 toward the trocar 63 according to an algorithm, as described further herein. In one variation, the sensor system 47 can be activated by the processor prior to or independently of the action of the switch 61, and the switch 61 can be used to signal the processor to begin calculations based on the signals received from the sensor system 47 to determine the estimated pose of the trocar and then affect guidance of the robotic arm 19 and its coupled tool drive 23. The switch 61 can be have one of several different configurations, e.g., a mechanical button and mechanical switch combination may be preferred but another form of tactile interface or a touchscreen is also possible, that can be activated by a user. Such placement of the switch 61 on or near the docking interface 27 allows an operator to activate a docking process without the need to travel away from the robotic arm 19 to a separate control interface, for example, the user control 2 that is located away from the robotic arm 19/tool drive 23.

While the sensor boards 49, 51 have been generally described as respective first and second printed circuit boards (PCBs) including the respective sensors 55, 57 embedded therein or thereon, it will be understood that the sensor system 47 can be provided in a different arrangement, for example, as discrete components, without departing from the disclosure. Additionally, it will be understood that any of the components described herein can be in communication via wired and/or wireless links, using any suitable ones of a variety of data communication protocols.

Referring additionally to FIGS. 6-9, guidance and docking of the docking interface 27 of the tool drive 23 with a trocar 63 that is at least partially inserted into the patient 6 is illustrated according to one aspect of the disclosure. The trocar 63, as shown, includes a generally tubular body 64 with a flanged upper portion or head 67 and an attachment portion 69 that protrudes from the head 67 for mating with the docking interface 27. In one variation, the attachment portion 69 can be configured, for example, as having a nose or collar or pin-like arrangement, and can have one or more surface features, e.g., notches, ridges, protrusions, angles, hooks, etc., for interengaging the receiver 37 of the docking interface 27.

The trocar 63 can have a different arrangement without departing from the disclosure. The trocar 63 includes a first magnet 71 and a second magnet 73 producing respective magnetic fields B1, B2 with known properties, e.g., known axes of polarization or angles therebetween, known dipole moments, known positions with respect to each other, etc. The first magnet 71 and the second magnet 73 each can have a different axis of polarization, e.g., an axis extending between opposite poles of the respective magnets 71, 73. In this regard, the first magnet 71 and the second magnet 73 may be obliquely arranged relative to one another, e.g., such that an angle is disposed between the respective axes of polarization. One or both of the magnets 71, 73 can be embedded in or otherwise coupled to the trocar 63, for example, by being integrally molded therein, by being inserted into a receiving portion thereof, or by being otherwise secured to the trocar 63. In one variation, the magnets 71, 73 are integrally formed in the attachment portion 69 of the trocar 63. In other variations, the magnets 71, 73 can be coupled to or embedded in a different portion of the trocar 63. While the trocar 63 is described as having the pair of magnets 71, 73, it will be understood that the trocar 63 can have a different number of magnets, e.g., provided as multiple pairs or singly-arranged magnets, without departing from the disclosure. In one variation, the trocar 63 can include a single magnet.

Still referring to FIGS. 6-9, and with additional reference to the process flows of FIGS. 10 and 11, a method for docking the robotic arm 19 to the trocar 63 according to aspects of the disclosure will be described and shown. The robotic arm 19 and docking interface 27, in a first or parked or unknown pose, is a pose in which the docking interface 27 is positioned a distance away from the magnets 71, 73 in the attachment portion 69 of the trocar 63 and respective magnetic fields B1, B2 generated therefrom such that a closer distance between the docking interface 27 and the trocar 63 is desirable to facilitate effective receipt or sensing of the magnetic fields B1, B2 by the sensors 55, 57. The parked or unknown pose of the robotic arm 19 can be, for example, a stowed arrangement of the robotic arm 19.

The docking interface 27 can be directed, guided, or driven to a second or entry position that is proximate, but physically separate from, the trocar 63, for example, manually by an operator (e.g., such that the robotic arm 19 is manually forced or manually guided by the hand of the operator) or via the robotic arm actuators 17. A suitable proximity of the docking interface 27 relative to the trocar 63 in which the sensors 55, 57 of the sensor system 47 can effectively sense or measure the magnetic fields B1, B2 can be indicated, for example, with an audible beep or audible alarm, an indicator light or other visual indicia, or a tactile indicator such as haptic or vibratory feedback on a portion of the robotic arm 19 or tool drive 23. In this regard, the sensors 55, 57 can be activated by the processor, for example, upon an initial setup or preparation of the robotic arm 19 and the tool drive 23, or via an input by an operator, prior to positioning of the robotic arm 19/tool drive 23 at the entry position. As shown at block 103, if the docking interface 27 is not in suitable proximity to the sensor system 47 to effectively sense the magnetic fields B1, B2, e.g., at the entry pose, the robotic arm 19 can be further guided toward the trocar 63, for example, by manual forcing or guidance by the operator, automatically under control of the processor, or some combination thereof, until determination by the processor that the docking interface 27 is positioned to effectively sense the magnetic fields B1, B2.

Figure 7:
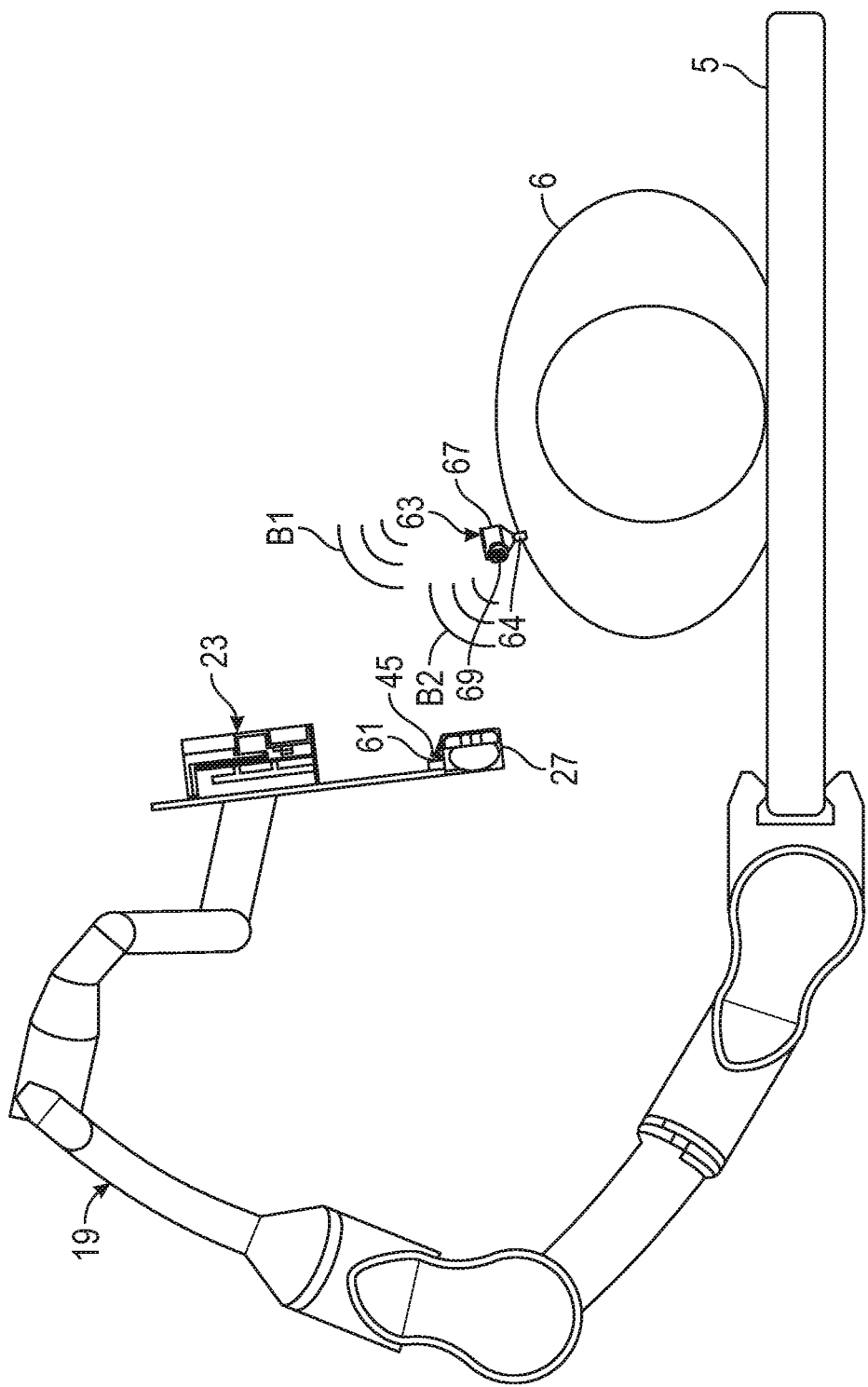

In the entry position shown in FIG. 7, the sensors 55, 57 of the sensor system 47 can sense the magnetic fields B1, B2 emanating from the trocar 63 and produce corresponding electrical signals that are communicated to the processor in the control tower 3. At such positioning of the robotic arm 19/docking interface 27 at the entry position, the processor can begin to calculate a position and orientation of the trocar 63 relative to the docking interface 27 based upon signals received from the sensor system 47 according to an algorithm. The initialization or start of such algorithm can be prompted, for example, by activating the switch 61. In one variation, the switch 61 can be activated by moving the lever 45 rearwardly into the unlocked (rearward) position such that the lever 45 contacts and actuates the switch 61.

Figure 10:
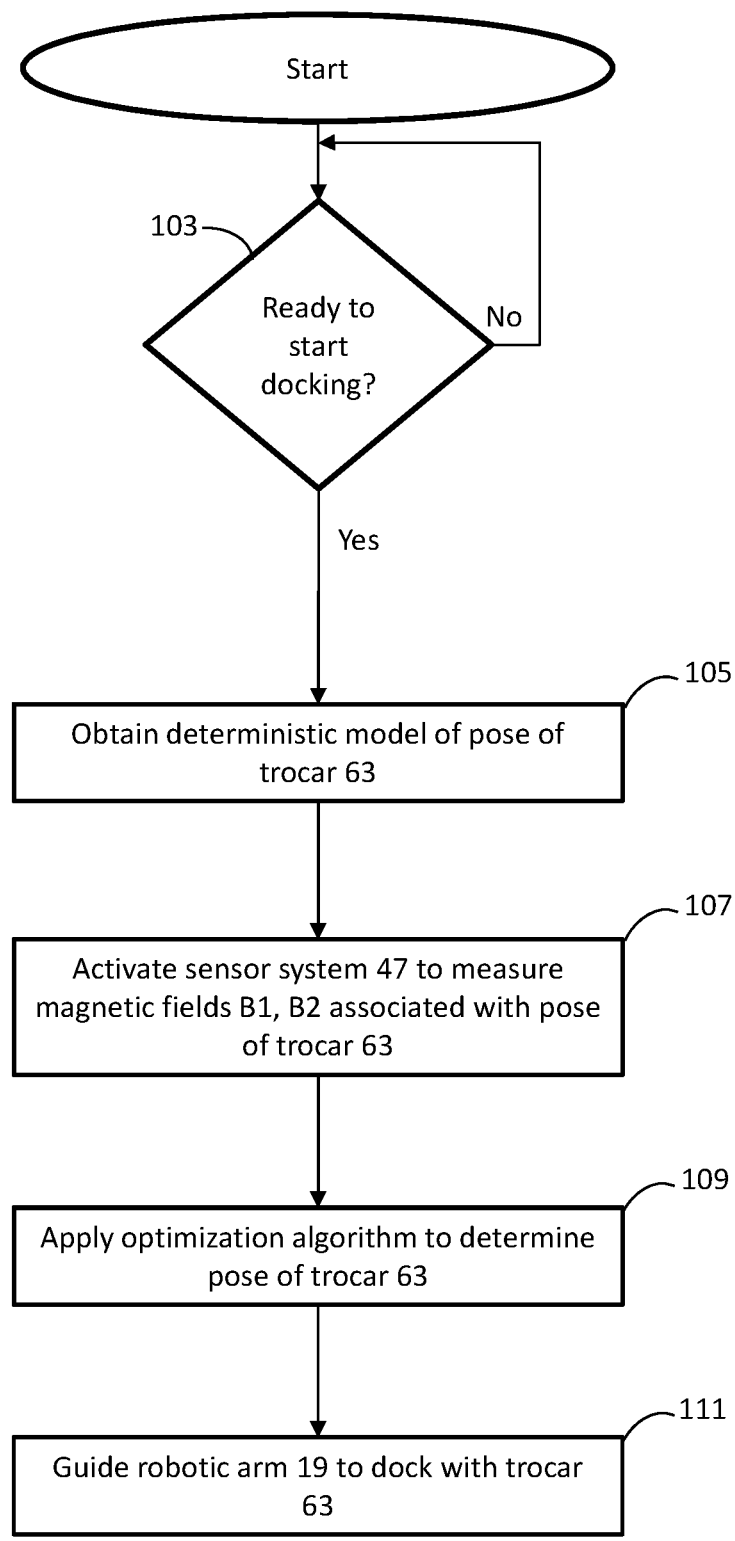
FIG. 10 is a process flow of a method for docking a tool drive attached to a robotic arm of a surgical robotic system to a trocar according to one aspect of the disclosure.
Figure 11:
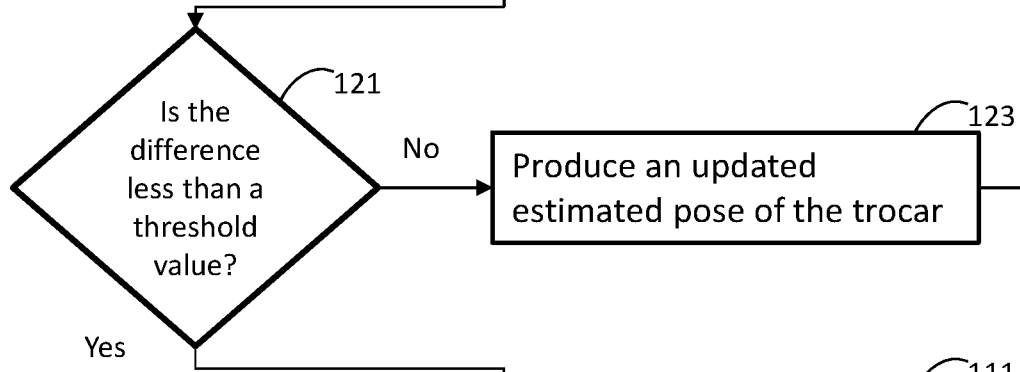
FIG. 11 is a process flow of a method for docking a tool drive attached to a robotic arm of a surgical robotic system to a trocar according to one aspect of the disclosure.

Accordingly, and with reference to block 107 in FIGS. 10 and 11, the processor in the control tower 3 is signaled by the switch 61 to apply an algorithm to determine the pose, e.g., spatial position and orientation, of the attachment portion 69 of the trocar 63 relative to the docking interface 27 to provide a transform, e.g., a transformation matrix, that can be used to guide or drive the robotic arm 19, and the docking interface 27 of the tool drive 23 attached thereto, toward the trocar 63. Such algorithm or set of algorithms can be a set of computer-implemented instructions, e.g., as part of a computer program product, firmware, etc., that can be stored on a non-transitory computer-readable medium for processing by a processor of the control tower 3, and will be collectively referred to as an algorithm herein. The initialization of the algorithm by the processor can be considered a start of a docking procedure of the robotic arm 19/tool drive 23.

In one variation, and according to the algorithm, the processor in the control tower 3 measures a sensed pose of the attachment portion 69 of the trocar 63 with respect to a 3-axis coordinate system, such as a system of X-, Y-, and Z-axes, by measuring and coordinating the electrical signals output by the sensors 55, 57 of the sensor system 47 to determine the relative strength of the magnetic fields B1, B2 of the respective magnets 71, 73 received at different locations, e.g., depths D1, D2, D3, D4, on the sensor boards 49, 51. For example, if the sensors 55, 57 in the column C1 output electrical signals corresponding to the received magnetic fields B1, B2 that is greater than the output electrical signals of the sensors 55, 57 in the column C2, a determination of a depth distance, e.g., an X-axis location, between the attachment portion 69 of the trocar 63 and the docking interface 27 can be calculated. Similarly, if the sensors 55, 57 in the row R1 output electrical signals corresponding to the received magnetic fields B1, B2 that is greater than the output electrical signals of the sensors 55, 57 in the columns R2, a determination of a vertical distance, e.g., a Z-axis location, between the attachment portion 69 of the trocar 63 and the docking interface 27 can be calculated. Furthermore, if the sensors 55 on the sensor board 49 output electrical signals corresponding to the received magnetic fields B1, B2 that is greater than the output electrical signals of the sensors 57 on the sensor board 51, a determination of a horizontal distance, e.g., a Y-axis location, between the attachment portion 69 of the trocar 63 and the docking interface 27 can be calculated. In one example, as the docking interface 27 is guided or driven along the one or more of the X-axis, the Y-axis, and the Z-axis, the generation of electrical signals by the sensors 55, 57 at the different depths D1, D2, D3, D4 can be used to determine when the trocar 63 becomes closer to the docking interface 27. In this regard, relative saturation of one or more of the sensors 55, 57 by the magnetic fields B1, B2, or degrees thereof, at different locations in the docking interface 27 can be used to determine the relative proximity of the docking interface 27 to the trocar 63.

The generation of differential electrical signals of sensors 55, 57 in different rows R1-R4 and different columns C1-C4 of the sensor boards 49, 51 can also be used by the processor in the control tower 3 to determine rotation about two or more of the X-, Y-, and Z-axes, e.g., roll, pitch, and yaw. For example, in the case of an asymmetrical relative saturation of the sensors 55, 57 by the magnetic fields B1, B2, e.g., such that the docking interface 27 is at least partially tilted with respect to the trocar 63, an orientation of the attachment portion 69 of the trocar 63 with respect to at least two of the X-, Y-, and Z-axes can be determined. In addition, the generation of electrical signals by the sensors 55, 57 can be compared by the processor to the known offset of the axes of polarization of the magnets 71, 73 to determine the rotation of the orientation of the attachment portion 69 of the trocar 63 about another of the X-, Y-, and Z-axes. In this regard, the arrangement of the sensors 55, 57 provides the processor in the control tower 3 with electrical signals corresponding to the magnetic fields B1, B2 according to the algorithm such that a real or sensed pose of the attachment portion 69 of the trocar 63 relative to the docking interface 27 can be determined with respect to six degrees of freedom (DOF): X-axis position, Y-axis position, Z-axis position, X-axis rotation, Y-axis rotation, and Z-axis rotation. In one variation, at least six measurements from the sensors 55, 57 can be used to determine the pose of the trocar 63. The accuracy and precision of the determination of the pose of the trocar 63 may correspond to a number of sensors 55, 57 that are employed in the sensor system 47 such that a desired number of sensors can be selected for use in the sensor system 47.

According to the algorithm, the processor in the control tower 3 can determine the sensed or measured pose of the trocar 63 based on the electrical signals produced by the sensors 55, 57 as described above. It will also be understood that the sensors 55, 57 on respective separate boards 49, 51 can provide comparable electrical signals corresponding to the magnetic fields B1, B2, for example, to reduce error such as electromagnetic noise provided by components of the surgical robotic system 1, for example, motors, actuators, displays, etc. Furthermore, one or more of the boards 49, 51 can incorporate inertial measurement units, for example, to compensate for the magnetic field of the Earth or vibrations of the robotic arm 19, such that associated motions of the robotic arm 19 that are not controlled by the algorithm can be minimized, inhibited, or prevented.

It will be understood that references to the pose of the trocar 63 herein are relative, specifically, to the sensor boards 49, 51 of the sensor system 47 that are mounted in the docking interface 27 of the tool drive 23. In this regard, an arrangement of the sensor boards 49, 51 relative to the surrounding docking interface 27 may be taken into account in determinations of the pose of the docking interface 27 described herein.

The algorithm applied by the processor in the control tower 3 can also produce estimated sensor readings that are output from a physical or deterministic model of the sensor system 47, e.g., a deterministic model of a position and arrangement of the sensor boards 49, 51 (see block 105 of FIG. 10). Such deterministic model of the sensor system 47 can be provided by the processor in the presence of a virtual representation of the magnetic fields B1, B2 that is modeled on the known properties of the magnets 71, 73, and which include the known relative offset of the respective axes of polarization of the magnets 71, 73. Accordingly, the deterministic model can be obtained or otherwise available to the processor (block 105 in FIG. 10) prior to the start of the algorithm described herein.

Such deterministic model can be a pre-defined function or set of functions applied by the processor that receive, as an input, an estimated pose of the trocar 63 relative to the modeled sensor system 47, e.g., relative to the sensor boards 49, 51. Accordingly, the estimated pose of the trocar 63 that is input to the deterministic model can be considered a selected pose (or initially, a guessed pose) of the trocar 63, and the deterministic model run by the processor produces, as an output, estimated sensor readings that correspond to this estimated pose of the trocar 63. In one variation, the estimated pose of the trocar 63 that is initially run through the deterministic model by the processor can be a stored set of values, e.g., predefined values, that can be based on typical trocar placements or arrangements that are known from historical data.

The estimated sensor readings produced by the processor from the deterministic model may be different from the measured sensor readings received by the processor from the sensor system 47 such that it can be desirable to reconcile the measured sensor readings with the estimated sensor readings, for example, to account for variables that may affect the accuracy of the measured sensor readings, such as magnetic fields generated by other trocars or other surgical equipment in the vicinity of the robotic arm 19, or other electromagnetic interference. Accordingly, the processor in the control tower 3 can compute a similarity measure in which the estimated sensor readings from the deterministic model are compared to the measured sensor readings from the sensor system 47, and can be optimized by the processor, e.g., iteratively updated to approach one another within a predetermined range or tolerance of error (see block 109 of FIG. 10).

At least blocks 115 through 123 of FIG. 11 illustrate the optimization algorithm of block 109 of FIG. 10, according to one aspect of the disclosure. The optimization algorithm can incorporate an Interior-Point Algorithm with Analytic Hessian, a non-linear least-squares solver, or a different optimization algorithm. An initial estimated or guessed pose of the trocar 63 (block 115) is run through the deterministic model by the processor to produce estimated sensor readings (block 117 in FIG. 11). These are then compared by the processor to the measured sensor readings received from the sensor system 47 (block 119), and the processor calculates whether the difference between the estimated sensor readings and the measured sensor readings is within an acceptable range or tolerance of error (block 121). If the difference between the estimated sensor readings and the measured readings are not within the acceptable range or tolerance of error, the processor adjusts the guessed or estimated pose of the trocar 63 (block 123) resulting in an updated estimated pose of the trocar 63 that is run through the deterministic model by the processor to produce updated estimated sensor readings (repeating block 117). The difference between the updated estimated sensor readings and the measured sensor readings is then calculated by the processor (repeating block 119) to determine whether the difference between the estimated sensor readings and the measured sensor readings are within the acceptable range or tolerance of error (repeating block 121.) If such difference is not within the acceptable range or tolerance of error, the estimated pose of the trocar 63 is iteratively updated again (repeating block 123) and run through the deterministic model by the processor. This iterative optimization algorithm continues until a set of optimized or final updated estimated sensor readings are produced by the processor that are within the acceptable range or tolerance of error (the "yes" branch at the output of block 121.)

The final updated estimated sensor readings produced through the aforementioned optimization correspond to a "determined pose" of the attachment portion 69 of the trocar 63, which, along with a pose of the docking interface 27, provides a transform that can be associated with a target or planned trajectory for guiding or driving the robotic arm 19, as described further herein. In this regard, via optimization by the processor of the estimated sensor readings produced through the deterministic model and the measured sensor readings received from the sensor system 47, the surgical robotic system 1 is operable to discriminate between the magnetic fields B1, B2 that are representative of the pose of the trocar 63 and other magnetic fields or electromagnetic interference such as those produced by other trocars or other surgical equipment in the operating arena. In one variation, in the presence of multiple trocars, the surgical robotic system 1 can be configured to target and initiate magnetic sensing and docking of a given docking interface with a nearest trocar, and distinguish between the magnetic field produced by the nearest trocar and the magnetic fields produced by other trocars.

In a further operation performed by the processor, the final updated estimated sensor readings, which corresponds to the determined pose of the attachment portion 69 of the trocar 63, are compared to the pose of the docking interface 27, e.g., to provide a transform that is used to guide the docking interface 27 toward the trocar 63 (block 111 in FIG. 10.) In one variation, the pose of the docking interface 27 can be a known value, for example, as determined through a log of prior movements of the robotic arm 19 by the robotic arm actuators 17 or various other sensors of the surgical robotic system 1, e.g., a gyroscope, accelerometer, position encoders, etc. In another variation, the pose of the docking interface 27 can be considered a geometric center from which the robotic arm 19 can be guided or driven to translate or rotate to approach the trocar 63. Accordingly, and as shown in FIG. 7, the processor in the control tower 3 can provide a set of guidance or driving control signals to the robotic arm actuators 17 based upon the final updated estimated sensor readings, to provide a tracking planned trajectory for the robotic arm 19 and to effect guidance or driving of robotic arm 19 to position and orient the docking interface 27 into docking facing relation with the attachment portion 69 of the trocar 63 such that the docking interface 27 matches or has substantially the same orientation as the orientation of the attachment portion 69 in a third or corrected entry position. It will be understood that, in the third or corrected entry position, the docking interface 27 is positioned proximate, but separate from, the trocar 63, and that the docking interface 27 is oriented such that only a final translational guidance of the robotic arm 19/docking interface 27 toward the trocar 63 will be sufficient to accomplish docking of the docking interface 27 with the trocar 63 (block 111).

In one variation, according to the algorithm, manual guidance of the robotic arm 19/tool drive 23 toward the trocar 36 by a user can be influenced by a virtual spring modeled by the processor that simulates a spring constant from which a force that is proportional to an offset from a planned trajectory toward the trocar 63 is generated, for example, via the robotic arm actuators 17, to cause the robotic arm 19/docking interface 27 to return toward the planned trajectory and toward an alignment with attachment portion 69 of the trocar 63. In this regard, in the instance of an operator manually forcing the robotic arm 19/docking interface 27 toward the trocar 63, the operator may encounter a force generated by the virtual spring implemented by the processor that increases with increasing distance from the planned trajectory toward the trocar 63 that is based upon the final updated estimated sensor readings. In this regard, the processor in the control tower 3 provides the planned trajectory as a virtual fixture, deviation from which results in corrective movements of and forces exerted on the robotic arm 19 by the robotic arm actuators 17 which tend to return the robotic arm 19/docking interface 27 toward an alignment with the planned trajectory. Additionally or alternatively, guidance of the robotic arm 19/docking interface 27 along the planned trajectory can be actively assisted by the robotic arm actuators 17 under control of the processor, e.g., to augment or amplify manual forces applied by an operator in manually guiding the robotic arm 19. Providing such a virtual fixture can significantly reduce effort by an operator in moving and maintaining alignment of the robotic arm 19/docking interface 27 with the planned trajectory.

In still another variation, fully manual forcing or guidance of the robotic arm 19, e.g., in which substantially no movement of the robotic arm 19 is effected by the robotic arm actuators 17 under processor control, can be optionally implemented as an alternative to automated driving of the robotic arm 19 by the robotic arm actuators 17 under processor control as described above, or as an alternative to the processor-controlled assistance or resistance by the robotic arm actuators 17 of an operator's manual guidance of the robotic arm 19 according to the virtual spring as described above. Switching between full or partial processor control of the robotic arm 19 via the robotic actuators and manual control of the robotic arm 19 by an operator can be effected, for example, by a control located on or near the docking interface 27 that is in electronic communication with the processor, for example, a switch, toggle, or other control, such as a foot pedal located proximate the table 5.

In processor controlled resistance or assistance of an operator's manual guidance of the robotic arm 19 as described above, or via the robotic arm actuators 17 or in fully manual guidance of the robotic arm 19 as described above, the positioning of the robotic arm 19/docking interface 27 relative to the planned trajectory provided by the processor can be provided to an operator, for example, with an audible beep or audible alarm, an indicator light or other visual indicia, a graphical indicator provided at the user console 2, or a tactile indicator such as haptic or vibratory feedback on a portion of the robotic arm 19, to assist an operator's manual guidance of the robotic arm 19.

In one aspect of the disclosure, as referred to by block 111, the processor in the control tower 3 can activate the robotic arm actuators 17 to guide or drive the robotic arm 19 according to the transform (based upon the final updated estimated sensor readings), such that the docking interface 27 is guided or driven toward the determined position and orientation of the trocar 63. It will be understood that this driving or guidance of the robotic arm 19 may include re-positioning of the docking interface 27 (according to the transform), and in some instances re-orienting the docking interface 27 (according to the transform) to achieve a corrected entry pose. Such guidance can be effected by the processor either simultaneously or as separate sequential steps.

Figure 12A:
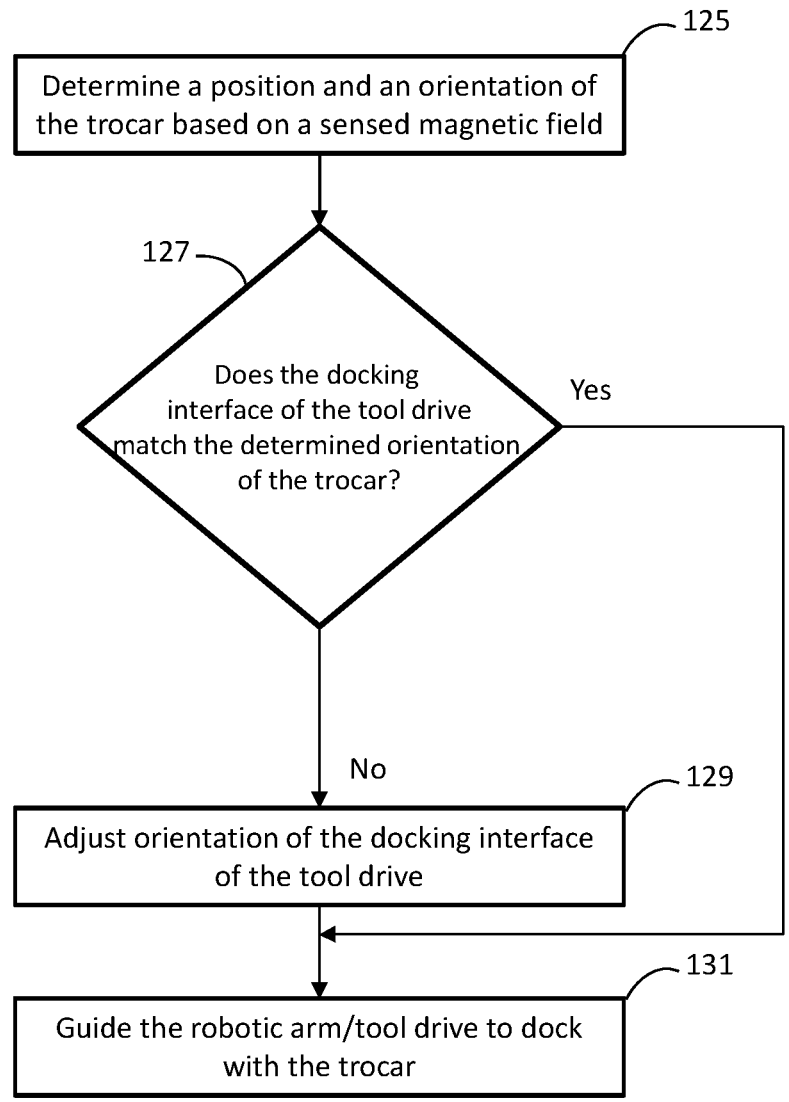
FIG. 12A is a process flow of a method for docking a tool drive attached to a robotic arm of a surgical robotic system to a trocar according to one aspect of the disclosure.

FIG. 12A illustrates the situation where during guidance or driving of the robotic arm 19 by the robotic arm actuators 17 based on the transform produced from the final updated estimated sensor readings, the processor can periodically or continuously check the pose of the docking interface 27, e.g., to confirm whether the docking interface 27 has reached or matches the entry pose, i.e. the orientation of the docking interface 27 substantially matches the determined pose of the trocar 63 (block 127). If the processor determines that the docking interface 27 does not match the orientation of the trocar 63, the processor can control the robotic arm actuators 17 to further drive or guide the robotic arm 19 toward such orientation (block 129). Once the orientation of the docking interface 27 substantially matches the orientation of the trocar 63, the processor can drive the robotic arm actuators 17 to further drive or guide the robotic arm 19, e.g., only in a translation movement (no need to now change the pose or orientation), until the tool drive 23 docks with the trocar 63 (block 131 in FIG. 12A).

Figure 8:
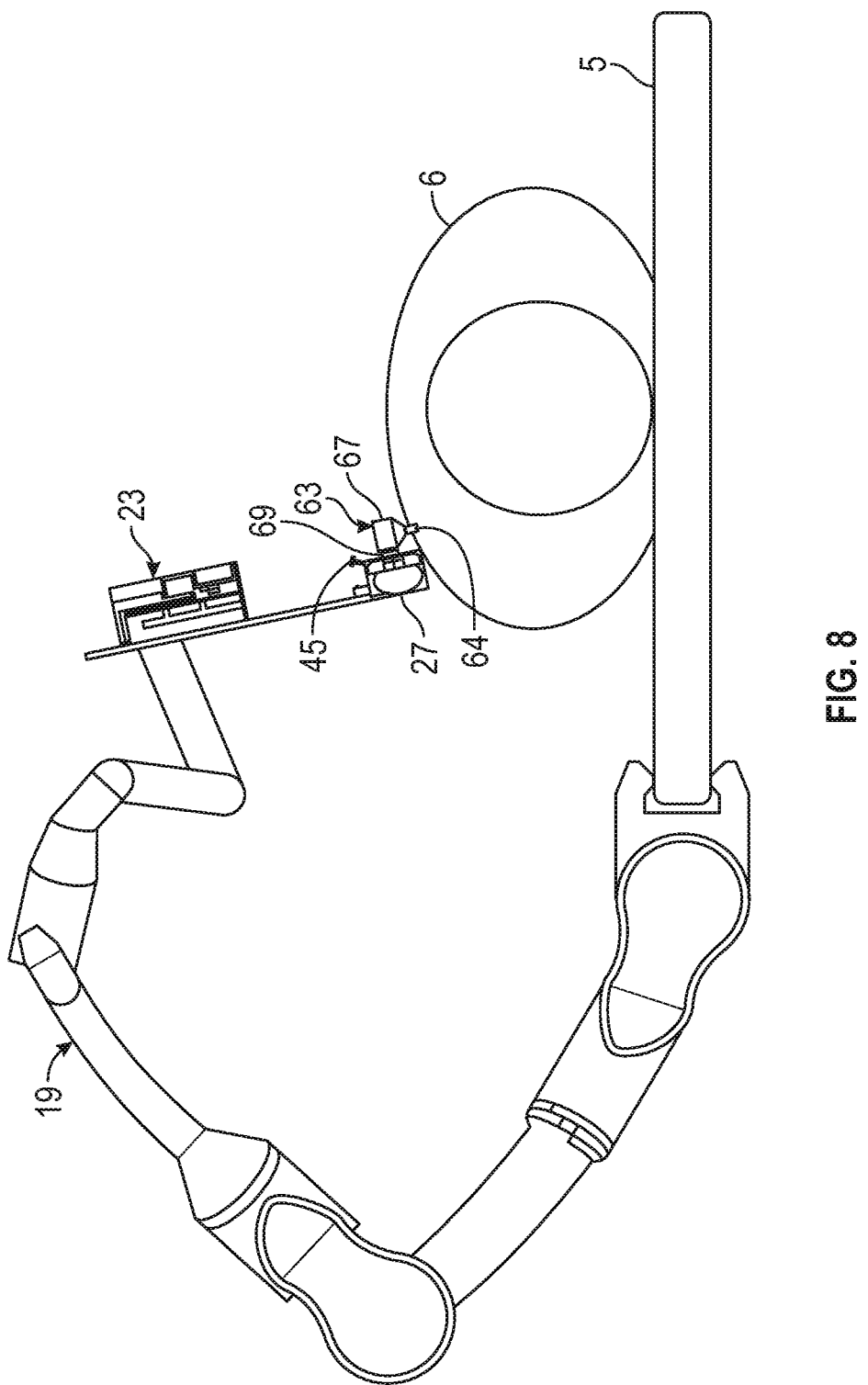
Figure 9:
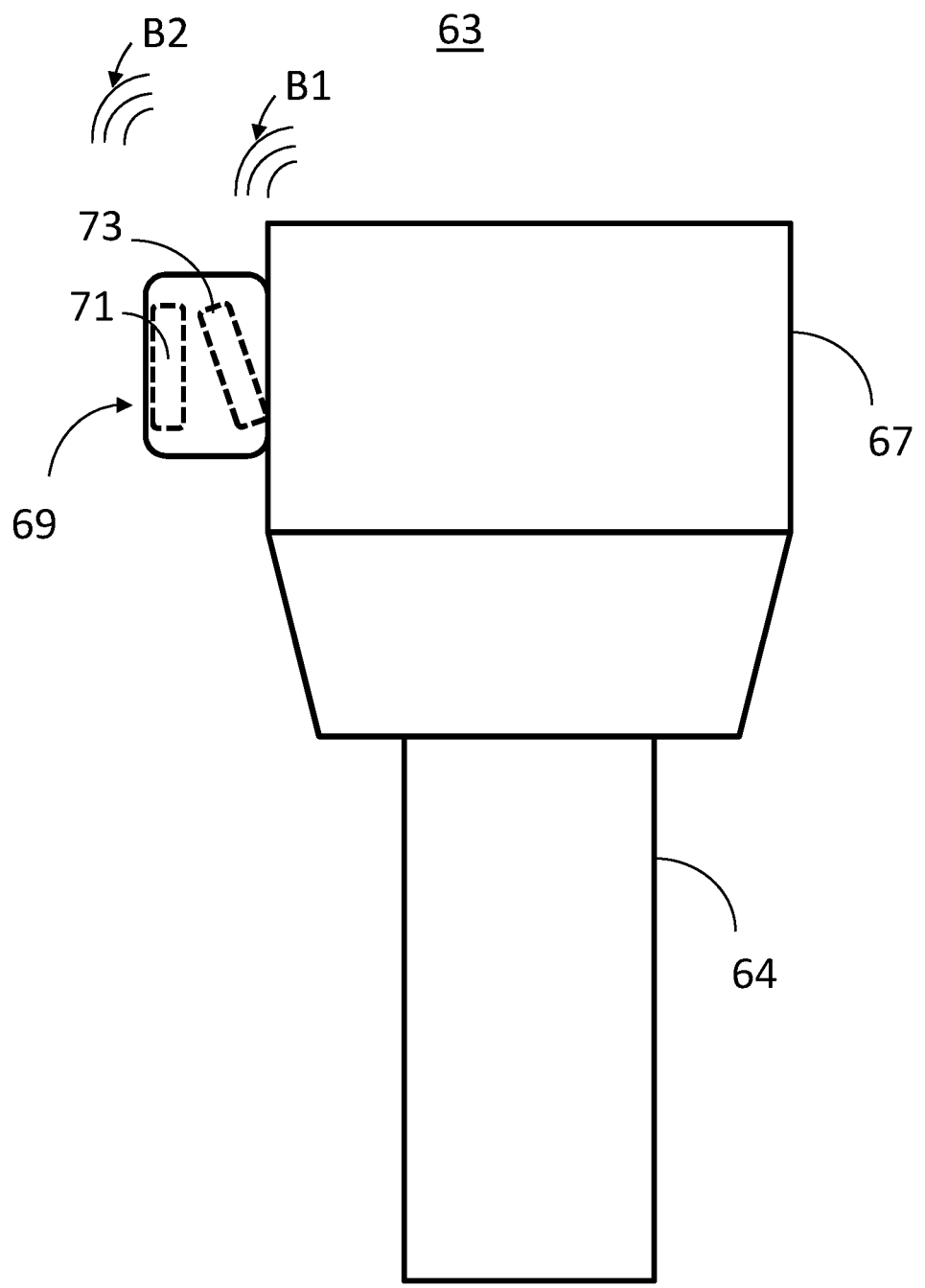
FIG. 9 is an enlarged schematic of the area 9 identified in FIG. 6.
Figure 12B:
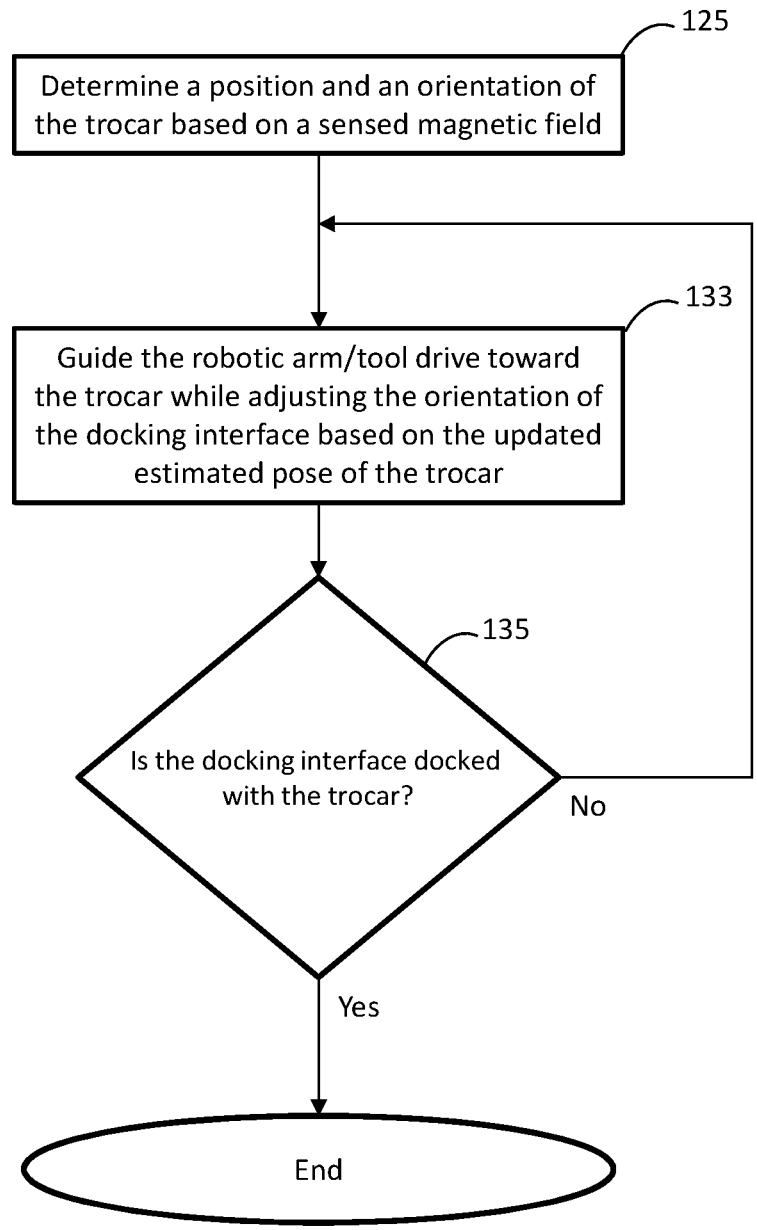
FIG. 12B is a process flow of a method for docking a tool drive attached to a robotic arm of a surgical robotic system to a trocar according to one aspect of the disclosure.

Still referring to FIGS. 7 and 8, and with additional reference to FIG. 12B, these figures serve to illustrate a docking process of the tool drive 23 (coupled to the robotic arm 19) with the trocar 63, according to one aspect of the disclosure in which both the orientation and the position of the docking interface are being adjusted while guiding the robotic arm in block 133.

FIG. 12B also serves to illustrate the last phase of the docking process in block 135 where the processor determines whether the docking interface 27 is positioned in a fourth or docked state, e.g., where the attachment portion 69 of the trocar 63 is at least partially surrounded or received in the receiving space 38 of the receiver 37. For the process in FIG. 12B, the processor in block 135 also checks whether the docking interface 27 and the trocar 63 have substantially the same orientation (and if not then the process loops back to block 133.) Contrast this with the process of FIG. 12A where the orientation of the docking interface has been finalized in block 129, before translating the docking interface in block 131 until the docked state is reached. In both cases, the docked state may refer to at least partial receipt of the attachment portion 69 of the trocar 63 in the receiving space 38 of the receiver 37, which can be determined by the processor, for example, based on feedback signals from the arm actuators and sensors translating into the pose of the robotic arm 19/docking interface 27 matching the final updated estimated sensor readings, e.g., such that the values are within an acceptable predetermined range of tolerance or error of each other. The processor can alert a user of this docked state by, for example, signaling an audible beep or audible alarm, an indicator light or other visual indicia, or a tactile indicator such as haptic or vibratory feedback on a portion of the robotic arm 19. In one variation, docked state of the docking interface 27 with the trocar 63 can be visually confirmed by an operator. If the docking interface 27 has been determined by the processor not to have docked with the trocar 63, the process in FIG. 12B loops back to block 133 where the processor can drive the robotic arm actuators 17 to further guide or drive the robotic arm 19 until docking of the tool drive 23 with the trocar 63 is achieved.

Such guidance or driving of the robotic arm 19 into docking engagement with the trocar 63 can also be performed through the processor controlled assistance or resistance by the robotic arm actuators 17 of an operator's manual guidance of the robotic arm 19 according to a virtual spring as described above, or can be guided fully manually by an operator as described above.

In the docked state, the docking interface 27 can be physically locked, e.g., rigidly mechanically coupled, with the trocar 63, for example, via the clamp components 33, 35, as described further below. In one variation, the state in which the attachment portion 69 of the trocar 63 is at least partially surrounded or received in the receiving space 38 of the receiver 37 can be considered as a ready to dock state, and the locked or mechanically coupled engagement of the docking interface 27 can be considered a docked or finally docked state.

Upon such positioning of the attachment portion 69 of the trocar 63 in the receiving space 38 of the receiver 37 of the docking interface 27, the lever 45 can be moved, e.g., manually or through an actuator under processor control, to a forward locked position to urge the clamp component 33 (FIG. 4) into pressible engagement with the attachment portion 69 of the trocar 63 such that the attachment portion 69 is secured, e.g., latched, clamped or locked, to the docking interface 27 in the docked position. Furthermore, the lever 45 can be moved rearwardly to the unlocked position to disengage the clamp component 33 from the attachment portion 69 to uncouple the robotic arm 19/docking interface 27 from the trocar 63.

Once the trocar 63 is locked to docking interface 27, one or more surgical tools can be coupled to the tool drive 23 and inserted through the trocar 63 to access a body cavity of the patient 6 and perform subsequent surgical operations therein. The surgical robotic system 1 has the capability to uniquely identify each tool (endoscope and surgical instruments) as soon as it is attached and display the tool type and arm location, for example, on the display 15 at the user console 2. The corresponding tool functions are enabled and can be activated using the UID 14 and the foot-operated controls 13. The patient-side assistant can attach and detach the tools, as required, throughout the procedure. The surgeon seated at the user console 2 can begin to perform surgery using the tools controlled the UID 14 and the foot-operated controls 13. The system 1 translates the surgeon's hand, wrist, and finger movements through the UID 14 and the foot-operated controls 13 into precise real-time movements of the surgical tools.

The arrangement of the sensor system 47 and the robotic arm 19 controlled by the processor in the control tower 3 according to the aforementioned algorithm and using inputs from the sensor system 47 provides a positioning and/or guidance system for the surgical robotic system 1 that ensures a smooth, controlled approach of the robotic arm 19/docking interface 27 toward the trocar 63 and, optionally, a docking coupling of the trocar 63 with the robotic arm 19/docking interface 27 such that a rigid, e.g., stabilized, mechanical connection between the trocar 63 and the robotic arm 19/tool drive 23. In this regard, the robotic arm 19/tool drive 23 and the trocar 63 can be docked while substantially maintaining the pose of the trocar 63, for example, so as to minimize, inhibit, or prevent movement of the trocar 63 with respect to a patient and to maintain a stable pose of the trocar 63 for subsequent surgical operations. Such docked engagement can be achieved through the aforementioned interaction of the magnets 71, 73 and the sensor system 47 such that the docking coupling does not require, for example, visual (e.g., line-of sight) or powered sensors (e.g., to provide ultrasonic triangulation, inertial sensing, or electromagnetic tracking) associated with the trocar 63. In this regard, various accessories such as drapes, coverings, or other barriers can be employed without interfering with the interaction of the magnets 71, 73 and the sensor system 47. Furthermore, the trocar 63 is provided with a robust configuration that can, for example, withstand cyclic use, vigorous use, and/or sterilization procedures without interfering with the properties of the magnets 71, 73.

The foregoing description, for purposes of explanation, used specific nomenclature to provide a thorough understanding of the invention. However, it will be apparent to one skilled in the art that specific details are not required in order to practice the invention. Thus, the foregoing descriptions of specific aspects of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

What is claimed is:

1. A surgical robotic system, comprising: a robotic arm having a plurality of actuators; a tool drive coupled to a distal end of the robotic arm, the tool drive comprising a docking interface to receive a trocar; one or more sensors operable to sense a magnetic field generated by the trocar wherein the one or more sensors are coupled to the docking interface of the tool drive and the magnetic field is generated by a plurality of magnets embedded in the trocar; and one or more processors configured to: determine a position and an orientation of the trocar based on the sensed magnetic field, and drive the plurality of actuators to orient the docking interface to the determined orientation of the trocar, and guide the robotic arm toward the determined position of the trocar.

2. The surgical robotic system of claim 1, wherein the one or more processors are configured to guide the robotic arm by automatically controlling the plurality of actuators to drive the arm toward the determined position of the trocar.

3. The surgical robotic system of claim 1, wherein the one or more processors are configured to guide the robotic arm by automatically controlling the plurality of actuators to assist a user who is manually guiding the robotic arm toward the determined position of the trocar.

4. The surgical robotic system of claim 1, wherein when the robotic arm is manually guided by a user toward the determined position of the trocar, the one or more processors are configured to control the plurality of actuators so as to resist the user's manual guidance of the robotic arm when the user's manual guidance is directing the robotic arm away from the determined position of the trocar.

5. The surgical robotic system of claim 1, wherein the docking interface defines a chamber, and one or more clamp components are disposed in the chamber.

6. The surgical robotic system of claim 5, wherein the one or more clamp components is movably coupled to the docking interface and configured to move to secure an attachment portion of the trocar to the docking interface.

7. The surgical robotic system of claim 6, wherein the attachment portion of the trocar is a protrusion extending from an upper portion of the trocar.

8. The surgical robotic system of claim 6, further comprising a lever positioned on the docking interface, and wherein movement of the lever causes movement of the one or more clamp components.

9. The surgical robotic system of claim 8, further comprising a switch mounted on the docking interface that, when actuated, signals the one or more processors to determine the position and orientation of the trocar based on the sensed magnetic field and guide the robotic arm to dock with the trocar.

10. The surgical robotic system of claim 9, wherein the switch is positioned such that movement of the lever actuates the switch.

11. The surgical robotic system of claim 1, wherein the one or more sensors is a plurality of sensors in a chamber of the docking interface.

12. The surgical robotic system of claim 11, wherein the plurality of sensors in the chamber of the docking interface comprises at least three sensors positioned at respective different depths measured from a frontal opening of the docking interface.

13. The surgical robotic system of claim 1, wherein the one or more sensors comprises a first plurality of sensors coupled to a first sensor board and a second plurality of sensors coupled to a second sensor board, the first sensor board and the second sensor board are on opposite sides of a chamber of the docking interface.

14. The surgical robotic system of claim 1 wherein the one or more processors are configured to guide the robotic arm by guiding the docking interface toward the trocar until an attachment portion of the trocar is at least partially disposed in a chamber of the docking interface, wherein the attachment portion of the trocar is a protrusion extending from an upper portion of the trocar.

15. The surgical robotic system of claim 14, wherein guiding the docking interface comprises automatically re-orienting the docking interface by the plurality of actuators in the robotic arm controlled by the one or more processors.

16. The surgical robotic system of claim 1, wherein the docking interface comprises a lever operable to lock the trocar to the docking interface, and a switch mounted on the docking interface and communicatively coupled to the one or more processors.

17. The surgical robotic system of claim 16, wherein method further comprises:
the one or more processors responding to the lever moving in one direction into contact with the switch, by processing a measured sensor reading; and
locking the docking interface to the trocar in response to the lever moving in another direction.

18. A method performed by a surgical robotic system, the method comprising: determining a position and an orientation of a trocar based on a sensed magnetic field, wherein the magnetic field is generated by a plurality of magnets embedded in the trocar and sensed by one or more sensors that are coupled to a docking interface of a tool drive that is coupled to a robotic arm; driving a plurality of actuators of the robotic arm to orient the docking interface of the tool drive that is coupled to the robotic arm, wherein the docking interface is oriented to the determined orientation of the trocar; and guiding the robotic arm toward the determined position of the trocar.

19. The method of claim 18, wherein guiding the robotic arm comprises automatically controlling the plurality of actuators to drive the robotic arm toward the determined position of the trocar.

20. The method of claim 18, wherein guiding the robotic arm comprises automatically controlling the plurality of actuators to assist a user who is manually guiding the robotic arm toward the determined position of the trocar.

* * * * *